US012635977B2

(12) United States Patent
Gibson

(10) Patent No.: US 12,635,977 B2
(45) Date of Patent: May 26, 2026

(54) LOOSELY COUPLED PROBE POSITION AND VIEW IN ULTRASOUND IMAGING

(71) Applicant: Siemens Medical Solutions USA, Inc., Malvern, PA (US)

(72) Inventor: Eli Gibson, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 305 days.

(21) Appl. No.: 16/674,398

(22) Filed: Nov. 5, 2019

(65) Prior Publication Data
US 2021/0128108 A1 May 6, 2021

(51) Int. Cl.
*A61B 8/00* (2006.01)

(52) U.S. Cl.
CPC .......... *A61B 8/4245* (2013.01); *A61B 8/4461* (2013.01); *A61B 8/466* (2013.01); *A61B 8/483* (2013.01); *A61B 8/523* (2013.01); *A61B 8/54* (2013.01); *A61B 8/585* (2013.01)

(58) Field of Classification Search
CPC ....... A61B 8/4245; A61B 8/585; A61B 8/523; A61B 8/54; A61B 8/466; A61B 8/483; A61B 8/5223; A61B 8/4461
See application file for complete search history.

(56) References Cited

U.S. PATENT DOCUMENTS

| | | | |
|---|---|---|---|
| 2004/0019270 A1 | 1/2004 | Takeuchi | |
| 2005/0096538 A1* | 5/2005 | Chomas | G01S 15/8993 |
| | | | 600/437 |
| 2006/0176242 A1 | 8/2006 | Jaramaz | |
| 2007/0225553 A1 | 9/2007 | Shahidi | |
| 2008/0009722 A1* | 1/2008 | Simopoulos | A61B 8/08 |
| | | | 600/437 |
| 2010/0179428 A1 | 7/2010 | Pedersen | |
| 2014/0236001 A1 | 8/2014 | Kondou | |
| 2015/0134113 A1 | 5/2015 | Konietschke | |
| 2016/0262720 A1 | 9/2016 | Henderson | |
| 2017/0265846 A1 | 9/2017 | Sui | |
| 2017/0360402 A1 | 12/2017 | De Jonge | |
| 2017/0360403 A1 | 12/2017 | Rothberg | |
| 2020/0289096 A1* | 9/2020 | Aase | A61B 8/461 |

FOREIGN PATENT DOCUMENTS

WO      WO-2021069445 A1 *   4/2021   ........... A61B 8/0883

* cited by examiner

*Primary Examiner* — Hien N Nguyen

(57) ABSTRACT

An ultrasound scanner scans a patient. The scan data is checked for an optimal view as a subpart of the scan. Where the field of view does not include the optimal view, the scan is repeated with a different spatial extent. Where the field of view does include the optimal view, then the scan data for that optimal view is used to generate an image. Both the view and the overall or broader scan are controlled together so that a sonographer may place the transducer at an approximate location to still provide a precise view.

11 Claims, 3 Drawing Sheets

10 —— Broad Scan of Patient based on View ID

11 —— Search for View based on Scan Data and View ID

12 —— Determine Any Change in Context

13 —— Determine Scan Pattern

14 —— Broad Scan of Patient based on Change

15 —— Identify the View

16 —— Generate Image of the View

LOOSELY COUPLED PROBE POSITION AND VIEW IN ULTRASOUND IMAGING

BACKGROUND

The present embodiments relate to precision aiming in ultrasound scanning for a desired field of view. Acquiring high quality ultrasound images of unseen anatomy and minimizing imaging artifacts requires very precise positioning of an ultrasound transducer. The quality of images varies with the expertise of the user, and optimal imaging typically requires highly trained sonographers. Even experienced sonographers struggle with specifying and recognizing the optimal view, physically positioning the ultrasound transducer such that the optimal view is visible in the image, and, at the same time, positioning the transducer with appropriate contact and pressure to minimize artifacts. This problem is typically solved by training expert sonographers to acquire ultrasound images. Experts may not be available. Some ultrasound systems address this challenge by ultrasound scanning a three-dimensional (3D) volume so that the region of interest is likely included and then displaying a derived image, such as a 3D rendering of anatomy. The information for the optimal view may be obscured by inclusion of information from other locations in the rendering.

SUMMARY

By way of introduction, the preferred embodiments described below include methods and systems for ultrasound imaging. An ultrasound scanner scans a patient. The scan data is checked for an optimal view as a subpart of the scan. Where the field of view does not include the optimal view, the scan is repeated with a different spatial extent. Where the field of view does include the optimal view, then the scan data for that optimal view is used to generate an image. Both the view and the overall or broader scan are controlled together so that a sonographer may place the transducer at an approximate location to still provide a precise view.

In a first aspect, a method of ultrasound imaging is provided. An ultrasound imaging system scans a first volume of a patient. A transducer for the scanning is held at a first location during the scanning. The scan data of the first volume is searched for a first view. A change in a field of view for the transducer at the first location is determined to acquire data for the first view. The ultrasound imaging system scans a second volume of the patient having the changed field of view. The first view is identified from scan data from the second volume. An image for the first view is generated from the scan data based on the identification of the first view.

In a second aspect, a system is provided for ultrasound imaging. A transducer is connectable with transmit and receive beamformers. An image processor is configured to both determine a view for imaging and determine first scan data to be acquired in a scan by the transmit and receive beamformers using the transducers. The first scan data including data for the view and surrounding context data. The transmit and receive beamformers are configured to perform the scan, and the image processor is configured to generate an image of the view. A display is configured to display the view.

The present invention is defined by the following claims, and nothing in this section should be taken as limitations on those claims. Further aspects and advantages of the invention are disclosed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Ultrasound imaging is performed with loosely coupled probe position and image view. By only loosely coupling the transducer position to the acquired image view, the user may position the transducer approximately, with good contact pressure. A computational system precisely positions the ultrasound image view relative to the transducer and/or establishes a field of view that includes the image view.

Loosely coupled ultrasound (LCUS) enables more stable imaging by setting the acquired field of view relative to an external coordinate system (i.e., patient) instead of relative to the operator's hand. LCUS enables scanning modes that depend on stable imaging (e.g. Radio Frequency Time Series imaging). LCUS enables scanning modes that depend on image analysis (e.g. 'snapping' to a standard view). LCUS may lower the total cost of operations of the ultrasound scanner by reducing the required level of training for operators.

The control to provide context and the analysis to specifically identify a view given the context operate in conjunction to provide LCUS. In one embodiment, the improved stability and scanning modes are achieved by: an analysis component defining the view relative to objects being imaged, rather than the probe position; and a control component dynamically redefining the data or context information (e.g., field of view, orientation, or other acquisition characteristic) that is acquired. In another embodiment, image-analysis-based scanning modes are achieved by: using the analysis component to determine the optimal view based on transducer and sensor data; and using the control component to acquire data to produce the optimal view. The lower required training levels are enabled by the combination of improved stability to reduce the need for fine control of the probe and image-analysis-based scanning to reduce the need for precise identification of standard ultrasound planes.

Figure 1:
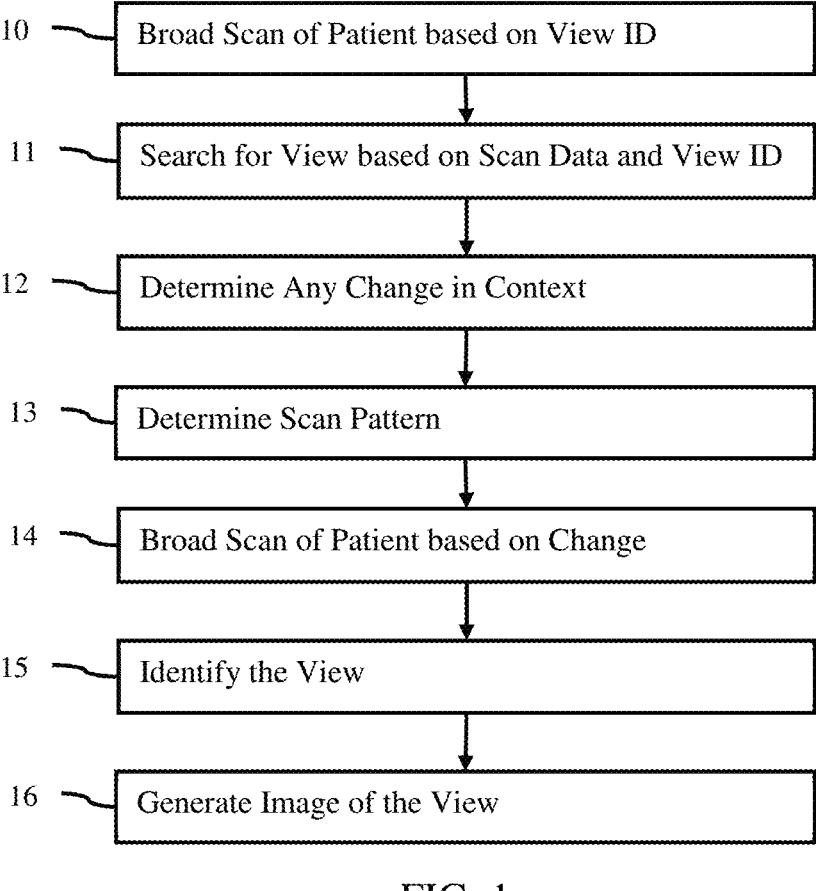
FIG. 1 is a flow chart diagram of one embodiment of a method for ultrasound imaging with an image frame of reference loosely related to a transducer frame of reference.

FIG. 1 shows one embodiment of a method of ultrasound imaging. In general, the user positions a transducer probe. Rather than manual aiming to get the desired view, a general position may be used. One process controls acquisition of sufficient context to identify the desired view, and another process identifies the view. An image of the desired view (e.g., standard view of the heart) may be generated without the user having to rotate, translate, and/or rock the transducer (e.g., the user does not have to adjust the location of the transducer since the image view is only loosely coupled to the transducer coordinate system).

Figure 4:
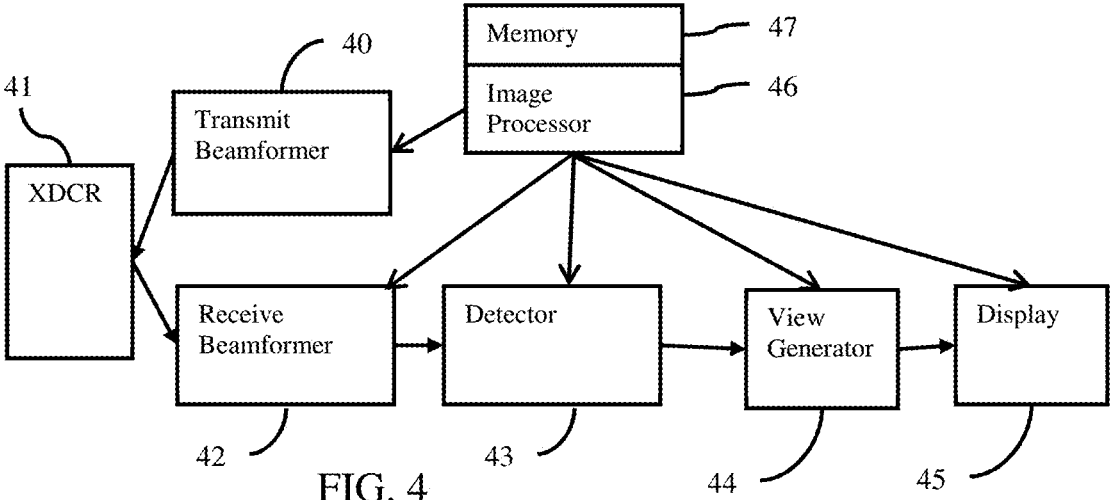
FIG. 4 is a block diagram of one embodiment of a system for ultrasound imaging using loosely coupled relation between imaging and transducer coordinates.

The method is performed by the system shown in FIG. 4 or a different system. For example, a medical diagnostic ultrasound imaging system scans in acts 10 and 14, an image processor searches in act 11, determines in acts 12 and 13, and identifies in act 15. The image processor and/or the imaging system generates the displayed image in act 16. Other devices may perform any of the acts, such as a beamformer controller performing acts 12 and/or 13.

The acts are performed in the order shown or another order. For example, acts 12 and 13 are performed in reverse order or simultaneously.

Additional, different, or fewer acts may be used. For example, act 13 is not performed. As another example, act 11 results in the identification of act 15, so acts 12-14 are not performed or are performed after repetition of act 10. Acts 12-14 may be performed regardless of results from act 11 where the control is separate from the analysis, merely using results from the searching. The acts 10-16 may be repeated for generating a series of images of a desired view.

In act 10, an ultrasound scanner or imaging system scans a patient. This scan is an initial scan but may be any scan in a sequence of on-going scans for examining a patient during a given imaging session or appointment. The initial scan may be the one occurring initially or before anatomy is detected in act 15, even if other previous scans occur before the initial scan. The scan may occur after anatomy was detected in act 15.

The scan is of a volume (i.e., a three-dimensional (3D) scan). The volume is a field of view established by the scanning configuration. The transducer and/or ultrasound scanner may be capable of other configurations, such as scanning a larger or different volume and/or volume at a different angle. The lateral extent and depth define the extent of the scanned volume, which extent is the field of view. Based on different settings, different size volumes may make up the scan volume. The user or the system determines the field of view and resulting scan volume. In alternative embodiments, a two-dimensional (2D) scan is performed. An area or planar region is scanned.

To scan a field of view with ultrasound, transmit and receive beams are formed by an ultrasound system. Any scan format, such as sector, linear, or Vector®, and corresponding field of view may be used. The scan lines are distributed by electric and/or mechanical steering in three-dimensions, providing data representing a volume (e.g., volume of N×M×R, where N, M, and R are integers greater than 1). Any three-dimensional format may be used, such as scanning sequentially along planes such that the scan planes together represent the volume. 2D scanning may be used.

The transmit and/or receive beam characteristics may be set or responsive to values of parameters. The depth and/or lateral extent of the field of view is set. Similarly, the transmit beam focal depth, transmit frequency, receive frequency, line density, sampling density, transmit waveform (e.g., number of cycles and/or envelope shape), frame rate, aperture, and/or other scanning characteristics are set. The number of transmit focal positions per scan line (e.g., one or two) may be set. Different, additional, or fewer scan (e.g., transmit and/or receive) parameters may be used.

Through receive beamformation, the responsive data represents samples in the field of view. Data received from the scanning is detected. A B-mode detector determines the intensity of acoustic echoes represented by the received data. For example, the receive data is formatted as in-phase and quadrature data. A square root of a sum of the squares of the in-phase and quadrature terms is calculated as the intensity. Other measures of the magnitude of the acoustic echo may be used for B-mode detection. In other embodiments, other types of detection and corresponding scans are performed, such as color flow (e.g., Doppler) estimation of velocity, power, and/or variance.

The values of the parameters for scanning are initially set using any process. In one embodiment, one or more of the parameters are set based on input by the user, predetermined values, and/or selection of an application or configuration. For example, the user selects volume or three-dimensional imaging of a particular anatomy, such as a heart valve. The user positions the transducer at a given location on the patient, such as between ribs for viewing the heart. Any location appropriate for imaging the anatomy of interest is used. Rather than requiring the expertise to then aim the transducer to obtain the correct field of view, acts 11 and 13 are performed to provide the view without requiring any or fine change in transducer position. During live or real-time imaging (scanning and outputting images at the same time or while the patient has a transducer placed against them), no special interaction is generally required or expected of the user other than applying the appropriate pressure of the transducer to the patient for imaging.

The ultrasound scanner is given a data acquisition specification that defines the data needed for (a) visualization, (b) optimal-view identification and (c) updating the controller context. The data includes scan data acquirable from the current transducer position. The acquisition specification indicates the application or purpose for the imaging, such as identifying a desired view or information to be obtained from imaging. The specification may indicate the default or other values for configuring the ultrasound imaging system for scanning. The scanner acquires ultrasound data according to the specification, and sends visualization data (e.g., what view is to be displayed and the scan data to generate the view) to the view components, view-identification data (e.g., what view is to be searched for and identified) to the analysis component, and context data (e.g., anatomy or region around the desired view to be used to identify the desired view) to the control component. In this instantiation, view-identification and context data could include a 3D or volumetric scan data, and the visualization data could include a specific 2D slice for the desired view. In another instantiation, the view-identification and context data could include a 2D or planar scan data, and the visualization data could include a specific region or area for the desired view. In yet another instantiation, the view-identification and context data include scan data from 2D or 3D scanning, and the visualization data includes an orientation or angle of scanning. Data from other sensors, such as a position sensor, may also be acquired. The other data is used to search for and/or identify the view.

In act 11, an image processor searches scan data for a view, such as searching for a 2D or 3D view from the scan data representing the volume of the patient. Other sensor data may be used in the search. An analysis component (e.g., instructions executed by the image processor or software module) performs the searching for and possible identification of the desired view from the acquired scan data.

The view may be a region representing specific anatomy or perspective of the anatomy. A sub-volume, sub-area, or 2D plane in a volume may be searched for and identified. Alternatively, the search is for an angle to view the anatomy, such as locating the anatomy and using a scan line orientation to scan the anatomy. Which view is optimal may be defined in various ways, depending on the clinical workflow. Examples include a view that corresponds to a standard anatomical ultrasound view or a temporal series of views that make up an evenly spaced 3D volume.

In one embodiment, the analysis component analyses the incoming view-identification data (e.g., identification of a standard view of the heart) to identify the optimal view. Based on the desired view (e.g., four chamber view), the data representing the view and/or the spatial position of the view relative to the field of view of the scan data is identified from the scan data being searched.

Image processing is used to search. For example, template matching is used. In other examples, landmarks may be detected and used to locate the view.

In one embodiment, the analysis component or search uses machine learning-based methods. A machine-learned model is trained to search for and identify the view. For example, a deep neural network is trained with deep learning. In one approach, the trained parameters take as input the full 3D scan data and outputs a parametric representation of an oriented oblique planar region within the volume. The parametric representation is a spatial definition of the location of the plane within the volume and/or with respect to the transducer. This view identification is output by the machine-learned network. The parameters of the network are optimized during training or system development on a dataset of many samples of 3D scan data and ground truth 2D optimal view pairs. In training, the error between the network predicted view and the optimal view defined a priori is minimized. The network is optimized such that for small changes to the transducer position (and therefore the 3D image), the optimal view, relative to the subject, would remain the same.

The search may locate the view. The partial area or volume (e.g., subset of the volume) may be located. For example, a spatial parametric representation of a planar region of the volume is identified from the searching. The view angle, plane, volume, and/or orientation are searched for and found. The identified view is found, providing the identification of act 15. Alternatively, the searching fails to locate the view, such as not locating a plane showing the anatomy of interest in the volume. Failure of the search, such as locating below a threshold probability, indicates insufficient context to locate the view in the current scan data. Additional scan data may be needed.

The parametric representation or other output of the searching and identification is sent to the control component and the view component. The control component uses the search results to control the scanning for providing context. The view component uses the search results with identification to generate an image from scan data for the identified view represented by the parametric representation.

In act 12, the image processor determines whether to change a field of view for the transducer as positioned at the location. The change is to provide sufficient context for identification of the desired view. A control component (e.g., instructions executed by the image processor or software module) performs the determination.

The search results are used to determine whether a change is needed. A partially or even fully identified view may benefit from additional context or inclusion of adjacent regions in the scan to better identify in subsequent analysis. The identified subset or other results are used to determine whether to change and what to change. The change in the field of view, orientation of scan lines, or other scan parameters is used to provide additional context for identification of the view. For example, the previous volume may not include one or more landmarks and/or part of the view, so the field of view of the volume is expanded or shifted (e.g., laterally and/or along range) to include the missing information used in identification. Changes in the orientation or other scan parameters may result in a different field of view.

Figure 2:
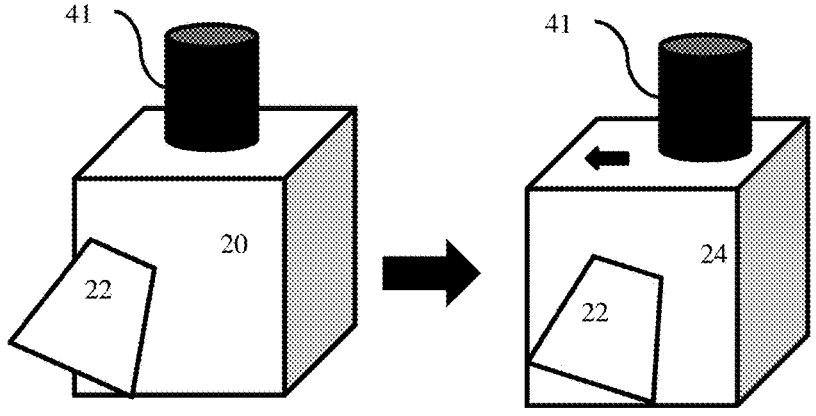
FIG. 2 illustrates one embodiment of adjusting the field of view to identify an optimal view.

FIG. 2 shows an example. The volume 20 is scanned in act 10 by the transducer 41. The search of act 11 identifies part of the desired view 22 in the volume 20. The part of the view 22 extending beyond the volume 20 is not detected. The control component shifts the scanning to scan a volume 24 more to one side of the transducer 41. This places the view 22 entirely within the volume 24 so that better identification of the view 22 may be performed. In alternative embodiments, the volume 20 is expanded and/or scan line orientation is changed.

In one embodiment, the control component determines the data to (a) create the requested view for the next frame. The change is to provide data to be used in generating the image in visualization. The control component determines the data to update the analysis component for the next frame. The change is to provide the data to be used in identification. The control component updates its own context and constructs an acquisition specification for the scanner.

If no scan data has been acquired, this acquisition specification may be based on system default settings. After sensor and/or ultrasound data has been acquired, this specification may be based on data acquired since the beginning of data acquisition or the last acquisition. For example, the control component specifies that the scanner should acquire the ultrasound lines that lie within the specified oblique plane for the visualization data and a volume of data to either side of this plane for view identification and context data whose width is based on estimated or expected probe motion.

In act 13, the image processor determines a scan pattern for subsequent scanning. In addition to the field of view and/or orientation, other acquisition parameters may be altered or set based on the desired context and/or view. The control component specifies how the data is to be acquired, such as specifying the beam-steering pattern and, for a mechanically actuated transducer, coordinating the transducer motion. For example, the waveform frequency, pulse repetition interval, scan line density, distribution of scan lines, type of scan (e.g., linear or sector), and/or other acquisition parameters are set to assist in identification without requiring movement of the transducer. The acquisition parameters to scan the volume of the patient again, such as a shifted or enlarged volume, are set. The user may move the transducer, intentionally or unintentionally. The subsequent scan may adjust the volume scanned and/or view to maintain the view despite the change in transducer position.

In act 14, the ultrasound imaging system scans the volume of the patient. This subsequent scan may be of the same volume as the previous scan, such as where the identification with sufficient confidence and context is made in the previous search. This subsequent scan may be of a different volume with or without overlap with the previous volume. The subsequent scan may have the changed field of view and/or acquisition parameter values to better capture context.

The transducer is maintained in the same location for the subsequent scan. Rather than requiring the user to fine tune the transducer position to acquire an image of the desired view, the transducer is maintained in position and the field of view is broad enough to locate the desired view as a subset. Unintentional motion of the transducer due to patient or sonographer motion may occur. The loosely coupled transducer-to-view allows for maintaining images of the desired view despite the unintentional motion while maintaining the transducer at the same location. In alternative embodiments, the change is to move the transducer, such as to rotate, rock, or translate the transducer to gather different context used for searching.

In act 15, the image processor identifies the view from scan data of the subsequently scanned volume. The search is repeated with the same or different context to identify the view in the scanned volume. The analysis component performs the search. When located due to searching, the view is identified. The spatial parametric representation is output when the view is identified.

The same analysis is used to identify from the subsequent scan as for the previous scan. For example, a machine-learned model identifies in response to input of the scan data for the subsequent volume and/or the previous volume. The output is the identification of the view, such as the location of the information of interest in the volume (e.g., location of a 2D plane or area).

In act 16, the image processor, using a display screen, generates an image for the identified view from the scan data. The image generated is based on the identification of the view. The entire view, where scan data is available, is imaged. Only part of the view may be imaged where only part is identified. The generated image has the view angle (e.g., for 3D rendering), plane, and/or orientation for the view. For an image of the entire view, less than all the scan data is used. The view is limited in one, two, or three dimensions to be less than the extent of the volume or area of the field of view.

The view component manipulates the scan data from the transducer to specify the image to be viewed on the ultrasound scanner. In one instantiation, this may entail setting the field of view and in-plane rotation relative to the acquired data to better conform to a standard view, as specified by the analysis component.

The images are B-mode images but may be other modes. Where the identification is of a view direction in 3D rendering, volume rendering is performed from the scan data at the identified view direction (orientation). The imaging is used for diagnosis and/or treatment guidance.

Figure 3:
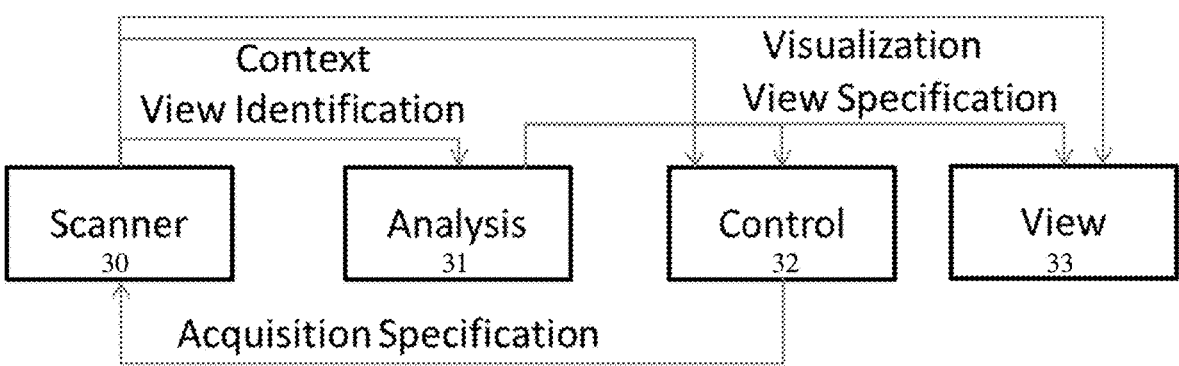
FIG. 3 illustrates example components and communications for loosely-coupled ultrasound imaging.

FIG. 3 shows one embodiment of components for performing the loose coupling of image and transducer. The components are implemented by the ultrasound imaging system, image processor, and/or other devices.

While shown as separate, any two or more of the components may be combined into one component. The components represent software modules (e.g., programs or sets of instructions) and/or devices. For example, the scanner component 30 and view component 33 are implemented by instructions for a medical ultrasound imaging system. As another example, the analysis component 31 and control component 32 are implemented by instructions for an image processor and/or beamformer controller.

FIG. 3 shows the components and communication for loosely-coupled ultrasound. An ultrasound scanner component 30 is capable of acquiring 2D or 3D scan data. Other sensors and sensor data, such as an ECG for triggering or transducer position sensor for transducer position determination, may be acquired and used in searching and identifying the desired view and/or context. The ultrasound scanner component 30 displays views from scanning. An analysis component 31 determines, based on scan data, sensor data, and/or view specification, the optimal view from the scan data. The control component 32 determines what data needs to be acquired to display the optimal view and determines the subsequent optimal view. A view component 33 constructs the view from the acquired data.

For communications, the scanner component 30 sends view identification data (i.e., indication of the desired view for an application) to the analysis component 31. The view identification data indicates what view is to be searched for and located. The view identification data contains information about the objects being imaged and the surrounding space. The scanner component 30 sends context data to the control component. The context data is the scan data and/or data from any other sensor. The context data may contain information about the objects being imaged and the surrounding space.

The analysis component 31 sends view specification data to the control component 32 and view component 33. The view specification data is the identified view. The located optimal view, such as values for the spatial representation parameterization, are communicated for determining context for subsequent scans and for display of an image of the view.

The control component 32 sends acquisition specification data to the scanner component 30. The acquisition specification data are the values for the acquisition parameters or information specifying the scan to be performed to acquire the desired context. The acquisition specification data defines what scan data to acquire.

The scanner component 30 sends visualization data to the view component 33. The visualization data is scan data for the identified view. The data to create the ultrasound image shown to the user is sent. Alternatively, the visualization data identifies the scan data, such as by memory location and/or spatial location, to be used for generating the image.

The user places the transducer. The components operate to identify and display an ultrasound image of the optimal view given the transducer placement. A stabilized view is provided without having to precisely position the transducer. An alternative instantiation allows the operator to change the view by switching between a stabilized mode and a free-moving mode using a physical control or software control. The free-moving mode links the imaged view to the transducer so that movement of the transducer moves the imaged view.

FIG. 4 shows one embodiment of a system for ultrasound imaging with loose coupling of the transducer coordinate system to the imaging region of the patient. The user configures the system for scanning and imaging, such as selecting an application for 2D imaging of specific anatomy. The user may alter values of one or more presets as desired. The user places the transducer 41 against the patient at an imaging window to scan a region of interest in the patient. Rather than requiring the user to move the transducer to attempt to locate a view of the desired anatomy once placed at or near the ideal location, the system locates the view from a broad scan, controls further scanning to provide context for continuing imaging, and generates images from the located view.

The system is an ultrasound imager. In one embodiment, the ultrasound imager is a medical diagnostic ultrasound imaging system. In alternative embodiments, the ultrasound imager is a personal computer, workstation, PACS station, or other arrangement at a same location or distributed over a network for real-time or post acquisition imaging.

The system implements the method of FIG. 1 or other methods. The system instantiates the components of FIG. 3 or other component arrangements. The system includes a transmit beamformer 40, a transducer 41, a receive beamformer 42, an image detector 43, a view generator 44, a display 45, an image processor 46, and a memory 47. Additional, different, or fewer components may be provided. For example, the receive beamformer 42 through the display 45 represents a B-mode processing path of an ultrasound imager. Other components may be provided in the path, such as a spatial filter, temporal filter, a scan converter, a mapping processor for setting dynamic range, or an amplifier for application of gain. As another example, a user input is provided.

The transmit beamformer 40 is an ultrasound transmitter, memory, pulser, analog circuit, digital circuit, or combinations thereof. The transmit beamformer 40 is configured to generate waveforms for a plurality of channels with different or relative amplitudes, delays, and/or phasing to focus a resulting beam at one or more depths. The waveforms are generated and applied to a transducer array with any timing or pulse repetition frequency. For example, the transmit beamformer 40 generates a sequence of pulses for different laterally and/or range regions. The pulses have a center frequency.

The transmit beamformer 40 connects with the transducer 41, such as through a transmit/receive switch. Upon transmission of acoustic waves from the transducer 41 in response to the generated waves, one or more beams are formed during a given transmit event. The beams are for B-mode or other mode of imaging. Sector, Vector®, linear, or other scan formats may be used. The same region is scanned multiple times for generating a sequence of images. The formed beams have an aperture, origin on the transducer 41, and angle relative to the transducer 41. The beams in the field of view have a desired line density and format. The transmit beamformer 40 steers the beams, so that tissue may be scanned at a given angle or orientation.

The transducer 41 is a 1-, 1.25-, 1.5-, 1.75- or 2-dimensional array of piezoelectric or capacitive membrane elements. The transducer 41 includes a plurality of elements for transducing between acoustic and electrical energies. For example, the transducer 41 is a one-dimensional PZT array with about 64-256 elements.

The transducer 41 connects with the transmit beamformer 40 for converting electrical waveforms into acoustic waveforms and connects with the receive beamformer 42 for converting acoustic echoes into electrical signals. The transducer 41 transmits the transmit beams where the waveforms have a frequency and are focused at a tissue region or location of interest in the patient. The acoustic waveforms are generated in response to applying the electrical waveforms to the transducer elements. The transducer 41 transmits acoustic energy and receives echoes. The receive signals are generated in response to ultrasound energy (echoes) impinging on the elements of the transducer 41.

The receive beamformer 42 includes a plurality of channels with amplifiers, delays, and/or phase rotators, and one or more summers. Each channel connects with one or more transducer elements. The receive beamformer 42 applies relative delays, phases, and/or apodization to form one or more receive beams in response to each transmission for detection. Dynamic focusing on receive may be provided. The receive beamformer 42 outputs data representing spatial locations using the received acoustic signals. Relative delays and/or phasing and summation of signals from different elements provide beamformation. In alternative embodiments, the receive beamformer 42 is a processor for generating samples using Fourier or other transforms. The sampling density by the receive beamformer 42 is for a range of depths. Timing is used to select the range of depths over which the sampling occurs. The receive beams have a desired scan line density at an orientation or orientations using an aperture.

The receive beamformer 42 may include a filter, such as a filter for isolating information at a second harmonic or other frequency band relative to the transmit frequency band. Such information may more likely include desired tissue, contrast agent, and/or flow information. In another embodiment, the receive beamformer 42 includes a memory or buffer and a filter or adder. Two or more receive beams are combined to isolate information at a desired frequency band, such as a second harmonic, cubic fundamental, or another band. The fundamental frequency band may alternatively be used.

The receive beamformer 42 outputs beam summed data representing spatial locations. Data for locations for a volume and/or sub-volume are output.

The detector 43 detects, such as detecting intensity, from the beamformed samples. Any detection may be used, such as B-mode and/or color flow detection. In one embodiment, a B-mode detector is a general processor, application specific integrated circuit, or field programmable gate array. Log compression may be provided by the B-mode detector so that the dynamic range of the B-mode data corresponds to the dynamic range of the display. The image detector 43 may or may not include a scan converter.

The view generator 44 is a renderer, such as a graphics processing unit, a scan converter, a display plane, and/or part of the image processor 46 for generating an image from scan data. Detected data is converted to a display format, mapped to display values, and otherwise used to generate an image for display on the display 45.

The above instantiation sends ultrasound data to the analysis and control components implemented or executed by the image processor 46. Other sensor data, such as inertial measurement unit data, transducer probe-mounted camera data, and/or ECG data, may be provided from one or more sensors. Scan data from the receive beamformer 42, detector 43, and/or view generator 44 is provided to the image processor 46 for analysis to search for and identify a view of interest and for control of the acquisition or scanning to provide the context for the search.

The image processor 46 interacts with the beamformers 40, 42, detector 43, view generator 44, and/or display 45. The image processor 46 is a beamformer controller, general processor, control processor, digital signal processor, application specific integrated circuit, field programmable gate array, digital circuit, analog circuit, combinations thereof, or another device for configuring the transmit and receive beamformers 40, 42.

The image processor 46 may use the memory 47 to acquire and/or buffer scan data and/or other information for view identification and control of scanning for context. The scan settings or values may be accessed by the beamformers 40, 42 and/or loaded from the memory 47 into buffers of the beamformers 40, 42 to configure the beamformers 40, 42. By loading values into registers or a table used for operation, the values of acquisition parameters used by the beamformers 40, 42 for imaging are set. Any control structure or format may be used to establish the imaging sequence. The beamformers 40, 42 are caused to acquire data for imaging at a frame rate, with a transmit focus, at an imaging frequency band, over a depth, with a line density, at a sample density, and/or line orientation. Different values of one or more acquisition or scanning parameters may result in a different frame rate, signal-to-noise ratio, penetration, contrast, field of view, and/or resolution.

The image processor 46 causes the beamformers 40, 42 to scan a volume of a patient. Any three-dimensional scan format may be used. Alternatively, a planar region or area of the patient is scanned (2D).

The image processor 46 is configured by software, firmware, and/or hardware to both determine a view for imaging and determine scan data to be acquired in a scan by the transmit and receive beamformers 40, 42 using the transducer 41. The image processor 46 accesses scan data from the receive beamformer 42, detector 43, and/or view generator 44. The accessed scan data includes data for the desired view and surrounding context data. Other data, such as from other sensors, may be accessed for searching for the desired view and controlling the context.

The image processor 46 is configured to determine whether the desired view is represented within any scan. The scan data of each scan in a sequence may be searched for locating the view. A view identification (i.e., which view is of interest) and the scan data from a given scan are used to locate the view. For each scan, the location is determined using the view identification and the scan data from that scan.

The image processor 46 is configured to determine the view using imaging processing, such as applying scan data as input to a deep machine-learned network. The view identification may be used to select the network to use or may be an input to the network for outputting the desired view.

To allow context for determining the view, the scan field of view extends beyond the bounds of the desired view. For example, a 2D scan may have a greater lateral or depth extent than used for the view. As another example, the scan is of a volume, and the view is a planar or area region within the volume.

The image processor 46 is configured to determine the scan data to acquire from the previous scan data and the view. The located view is used to determine any changes in the context, such as altering orientation, field of view, or other scan parameter.

For any frame or set of scan data for which the image processor 46 locates the view, the image processor 46 is configured to generate an image of the view. The locations of the view relative to the scan data and/or the scan data for the view are used to generate the image. The image processor 46 itself may generate the image. Alternatively, the locations and/or scan data are provided to or identified for the view generator 44 to generate the image. For example, the image processor is configured to determine the view as a spatial representation or parameterization representing a sub-part of the scan data from the previous scan. The scan data of this subpart is used to generate a B-mode, flow mode, and/or another imaging mode image.

The display 45 is a CRT, LCD, monitor, plasma, projector, printer or other device for displaying an image or sequence of images of the located view. Any now known or later developed display 45 may be used. The display 45 may display three-dimensional representations, such as rendered based on a view direction for the located view. The display 45 may display a two-dimensional image of a planar region corresponding to the view in other embodiments.

The image processor 46 operates pursuant to instructions stored in the memory 47 or another memory. The instructions configure the system for performance of the acts of FIG. 1. The memory 47 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method of ultrasound imaging, the method comprising:

scanning, by an ultrasound imaging system, a first volume of a patient, where a transducer for the scanning is held at a first location during the scanning providing a first view;

searching, by a machine-learned model, for an optimal view in the first volume, wherein searching comprises inputting, by the machine-learned model, the first volume and outputting, by the machine-learned model, search results that describe the optimal view, the machine-learned model trained on a dataset of pairs of data including 3D scan data and ground truth 2D optimal view data;

determining, based on the search results and the first view, a change in a field of view for the transducer to acquire additional data for the optimal view;

determining acquisition parameters for a subsequent scan without requiring movement of the transducer, the subsequent scan to acquire the additional data;

scanning, by the ultrasound imaging system while the transducer is held at the first location using the acquisition parameters, a second volume of the patient having the changed field of view, the second volume acquiring the additional data for the optimal view;

identifying the optimal view from the first volume and second volume; and generating an image for the optimal view.

2. The method of claim 1 wherein searching and identifying are performed by an analysis component and determining is performed by a control component.

3. The method of claim 1 wherein searching for the optimal view comprises locating the optimal view as a subset of the first volume, and wherein determining the change comprises determining the change based on the subset.

4. The method of claim 1 wherein searching for the optimal view comprises failing to locate the optimal view in the first volume, and wherein determining the change comprises expanding the first volume to the second volume or shifting the first volume to the second volume.

5. The method of claim 1 wherein the optimal view comprises at least one of a view angle, a plane, or an orientation, and wherein generating comprises generating the image with at least one of the view angle, the plane, or the orientation.

6. The method of claim 1 further comprising determining a scan pattern for scanning the second volume.

7. The method of claim 1 wherein determining the change comprises determining context for the identifying.

8. The method of claim 1 wherein scanning the second volume comprises scanning the second volume with the transducer in the first location.

9. The method of claim 1 wherein the scanning the first and second volumes in combination with the identifying comprises generating the image of the optimal view without requiring adjustment of the first location by a user.

10. A system for ultrasound imaging, the system comprising:

a transmit beamformer;

a receive beamformer;

a transducer connectable with the transmit and receive beamformers;

an image processor configured with a machine learning network configured to input a first volume from a previous scan using the transducer held at a first location and output search results that describe a view that was not captured in the previous scan, the machine learning network trained on a dataset of pairs of data including 3D scan data and ground truth 2D view data, the image processor further configured to determine, based on the search results a subsequent view for imaging and determine acquisition parameters for a subsequent scan using the transducer held at the first location, the subsequent scan to acquire additional data for the view by the transmit and receive beamformers using the transducer, the additional data including data for the view that was not captured during the previous scan and surrounding context data;

wherein the transmit and receive beamformers are configured to perform the subsequent scan using the transducer held at the first location to capture the additional data not captured during the previous scan, and the image processor is configured to generate an image of the view;

a display configured to display the view.

11. The system of claim 10 wherein the image processor is configured to determine the view as a plane.

\* \* \* \* \*